(12) United States Patent
Tanaka et al.

(10) Patent No.: US 12,285,930 B2
(45) Date of Patent: Apr. 29, 2025

(54) OPHTHALMIC SOLUTION CONTAINER

(71) Applicant: Fujimori Kogyo Co., Ltd., Tokyo (JP)

(72) Inventors: Yoshitoh Tanaka, Tokyo (JP); Yuuki Etou, Tokyo (JP); Toyoaki Suzuki, Tokyo (JP)

(73) Assignee: ZACROS Corporation, Tokyo (JP)

( * ) Notice: Subject to any disclaimer, the term of this patent is extended or adjusted under 35 U.S.C. 154(b) by 489 days.

(21) Appl. No.: 17/299,704

(22) PCT Filed: Dec. 6, 2019

(86) PCT No.: PCT/JP2019/047969
§ 371 (c)(1),
(2) Date: Jun. 3, 2021

(87) PCT Pub. No.: WO2020/116654
PCT Pub. Date: Jun. 11, 2020

(65) Prior Publication Data
US 2022/0055357 A1 Feb. 24, 2022

(30) Foreign Application Priority Data
Dec. 7, 2018 (JP) .................. 2018-230193

(51) Int. Cl.
*B32B 27/08* (2006.01)
*A61F 9/00* (2006.01)
(Continued)

(52) U.S. Cl.
CPC ............ *B32B 27/08* (2013.01); *A61F 9/0008* (2013.01); *B32B 1/00* (2013.01); *B32B 27/325* (2013.01);
(Continued)

(58) Field of Classification Search
CPC ......... B32B 27/08; B32B 1/02; B32B 27/325; B32B 2250/242; B32B 2250/40;
(Continued)

(56) References Cited

U.S. PATENT DOCUMENTS 3,749,620 A * 7/1973 Montgomery ...... B29C 66/1122
206/219
4,816,305 A * 3/1989 Stillwell .............. B65D 1/0215
428/36.6
(Continued)

FOREIGN PATENT DOCUMENTS

CN 101754742 A 6/2010
EP 2266521 A1 12/2010
(Continued)

OTHER PUBLICATIONS

Intellectual Property India Office Action for Application No. 202117025149 dated Sep. 15, 2022.
(Continued)

*Primary Examiner* — Donnell A Long
(74) *Attorney, Agent, or Firm* — Harris Beach Murtha Cullina PLLC

(57) ABSTRACT

An ophthalmic solution container has an accommodation part in which an ophthalmic solution is accommodated, and the accommodation part is composed of a laminate having a layer containing a cyclic olefin interpolymer (copolymer) and a layer containing a polyethylene resin provided outside the layer containing the cyclic olefin interpolymer (copolymer). The thickness of the layer containing the cyclic olefin interpolymer (copolymer) is 50 μm to 1,000 μm, and the thickness of the laminate is 300 μm to 2,000 μm. According to the container, it is possible to minimize sorption (adsorption and absorption) of the ophthalmic solution, it is possible
(Continued)

to improve moisture barrier properties and minimize evaporation, and it is also possible to reduce the squeeze strength.

4 Claims, 1 Drawing Sheet

(51) Int. Cl.
    *B32B 1/00*     (2006.01)
    *B32B 1/02*     (2006.01)
    *B32B 27/32*     (2006.01)
    *B65D 1/02*     (2006.01)
    *B65D 1/08*     (2006.01)

(52) U.S. Cl.
    CPC ............ *B65D 1/0215* (2013.01); *B65D 1/08* (2013.01); *B32B 2250/242* (2013.01); *B32B 2250/40* (2013.01); *B32B 2270/00* (2013.01); *B32B 2307/732* (2013.01); *B32B 2439/80* (2013.01)

(58) Field of Classification Search
    CPC .......... B32B 2270/00; B32B 2307/732; B32B 2439/80; B32B 27/32; B32B 2307/7246; A61F 9/0008; A61F 2210/0076; B65D 1/0215; B65D 1/08
    See application file for complete search history.

(56) References Cited

U.S. PATENT DOCUMENTS

| | | | |
|---|---|---|---|
| 8,377,029 B2 | 2/2013 | Nagao et al. | |
| 2002/0090473 A1* | 7/2002 | Lee | B65D 1/0215 |
| | | | 264/318 |
| 2004/0231666 A1* | 11/2004 | Barker | B32B 27/36 |
| | | | 128/200.23 |
| 2005/0031812 A1 | 2/2005 | Suzuki | |
| 2006/0165928 A1 | 7/2006 | Suzuki et al. | |
| 2011/0100861 A1* | 5/2011 | Manabe | A61J 1/067 |
| | | | 206/524.6 |
| 2015/0290080 A1* | 10/2015 | Weikart | A61J 1/062 |
| | | | 206/438 |
| 2020/0122898 A1* | 4/2020 | Ikeda | B65D 1/0207 |
| 2020/0171244 A1* | 6/2020 | Weikart | C23C 16/401 |

FOREIGN PATENT DOCUMENTS

| | | |
|---|---|---|
| JP | 2001001389 A | 1/2001 |
| JP | 2008104868 A | 5/2008 |
| JP | 2012135621 A | 7/2012 |
| JP | 2015016871 A | 1/2015 |
| WO | 9601184 A1 | 1/1996 |
| WO | 03043895 A1 | 5/2003 |
| WO | 2004080370 A1 | 9/2004 |
| WO | 2009113177 A1 | 9/2009 |
| WO | 2010062741 A1 | 6/2010 |
| WO | 2018190422 A1 | 10/2018 |

OTHER PUBLICATIONS

Chinese Search Report and Office Action dated Jun. 10, 2022 issued in Chinese Application No. 201980089179.3.
International Search Report dated Jan. 7, 2020 issued in PCT/JP2019/047969.

* cited by examiner

OPHTHALMIC SOLUTION CONTAINER

CROSS-REFERENCE TO RELATED APPLICATIONS

Priority is claimed on Japanese Patent Application No. 2018-230193, filed Dec. 7, 2018, the content of which is incorporated herein by reference.

FIELD OF THE INVENTION

The present invention relates to an ophthalmic solution container.

BACKGROUND OF THE INVENTION

In the related art, a resin container made of polyethylene (PE), polypropylene (PP), polyethylene terephthalate (PET) or the like is widely used as an ophthalmic solution container in which an ophthalmic solution is accommodated. A general ophthalmic solution container includes an ophthalmic solution accommodation part and a nozzle part protruding from the accommodation part, and has a configuration in which an ophthalmic solution can be instilled from the ophthalmic solution container by pressing the accommodation part with the fingers while the nozzle part faces the eye.

On the other hand, in a packaging container such as a packaging bag, cyclic olefin copolymers (copolymers) are known as resins having excellent non-adsorption properties with respect to contained components (for example, refer to Patent Literature 1 and 2).

[Patent Literature 1] WO 2003/043895
[Patent Literature 2] WO 2004/080370

SUMMARY OF THE INVENTION

Technical Problem

In order to minimize sorption (adsorption or absorption) of an ophthalmic solution in an accommodation part, it is necessary to use a material that is unlikely to sorb an active component of the ophthalmic solution. However, according to the studies performed by the inventors, it was found that, when cyclic olefin copolymers (copolymers) are used for a resin having excellent non-adsorption properties with respect to contained components in an ophthalmic solution container, since the cyclic olefin copolymers (copolymers) are harder than the above resins such as PE, PP, and PET, there is a problem that the squeeze strength required for an operation of pressing the accommodation part during instillation increases.

The present invention has been made in view of the above circumstances, and an object of the present invention is to provide an ophthalmic solution container in which it is possible to minimize sorption (adsorption and absorption) of the ophthalmic solution, it is possible to improve moisture barrier properties and minimize evaporation, and it is also possible to reduce the squeeze strength.

Solution to Problem

In order to solve the above problems, one aspect of the present invention provides an ophthalmic solution container having an accommodation part in which an ophthalmic solution is accommodated, the accommodation part being composed of a laminate having a layer containing a cyclic olefin interpolymer (copolymer) and a layer containing a polyethylene resin provided outside the layer containing the cyclic olefin interpolymer (copolymer), and the thickness of the layer containing the cyclic olefin interpolymer (copolymer) being 50 µm to 1,000 µm, and the thickness of the laminate being 300 µm to 2,000 µm.

The layer containing the cyclic olefin interpolymer (copolymer) may constitute an innermost layer of the accommodation part.

The accommodation part may have an innermost layer containing the polyethylene resin inside the layer containing the cyclic olefin interpolymer (copolymer).

The thickness of the innermost layer containing the polyethylene resin may be 500 µm or less.

The ophthalmic solution container may have a nozzle part for instilling an ophthalmic solution accommodated in the accommodation part.

The layer containing the cyclic olefin interpolymer (copolymer) may contain at least one of COPs (copolymers of different cyclic olefins) and COCs (copolymers of a cyclic olefin and an acyclic olefin). Advantageous Effects of Invention According to the ophthalmic solution container of the above aspect, when a layer containing a polyethylene resin is laminated outside a layer containing a cyclic olefin interpolymer (copolymer) having excellent non-sorption properties, it is possible to minimize sorption (adsorption and absorption) of the ophthalmic solution, improve moisture barrier properties and minimize evaporation, also reduce the squeeze strength, and improve squeeze properties.

DETAILED DESCRIPTION OF THE INVENTION

Hereinafter, the present invention will be described based on preferred embodiments.

An ophthalmic solution container of the present embodiment includes an accommodation part in which an ophthalmic solution is accommodated, and the accommodation part is composed of a laminate having a layer containing a cyclic olefin interpolymer (copolymer). In addition, the laminate constituting the accommodation part has a layer containing a polyethylene resin at least outside a layer containing a cyclic olefin interpolymer (copolymer).

Figure 1:
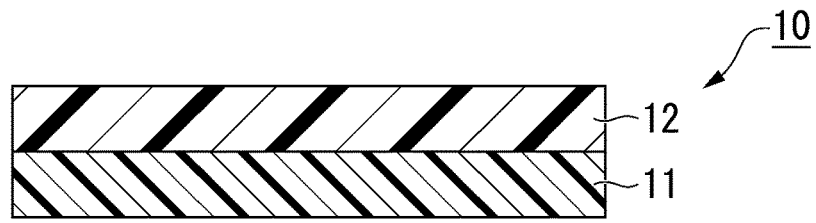
FIG. 1 is a cross-sectional view showing a laminate according to a first embodiment.

FIG. 1 shows a laminate of an accommodation part according to a first embodiment. A laminate 10 has a moisture-proof innermost layer 11 and an outer layer 12. The innermost layer 11 is composed of a layer containing a cyclic olefin interpolymer (copolymer). The outer layer 12 is composed of a layer containing a polyethylene resin. The innermost layer 11 has an inner surface that can come into contact with an ophthalmic solution. The outer layer 12 may be the outmost layer (layer that comes in contact with the outside air) of the laminate 10. The laminate 10 may have another layer outside the outer layer 12.

Figure 2:
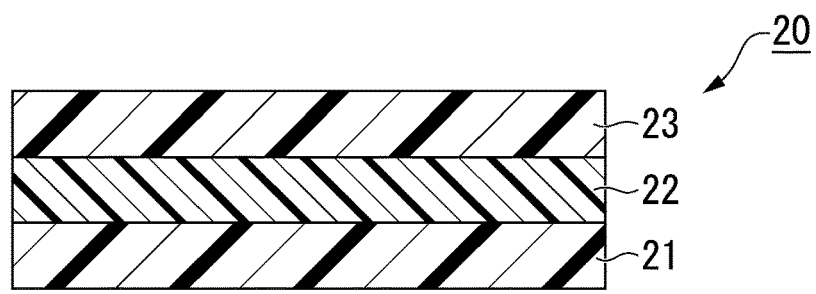
FIG. 2 is a cross-sectional view showing a laminate according to a second embodiment.

FIG. 2 shows a laminate of an accommodation part according to a second embodiment. A laminate 20 has an innermost layer 21, a moisture-proof intermediate layer 22, and an outer layer 23. The intermediate layer 22 is composed of a layer containing a cyclic olefin interpolymer (copolymer). The outer layer 23 is composed of a layer containing a polyethylene resin. The innermost layer 21 has an inner surface that can come into contact with an ophthalmic solution. The outer layer 23 may be an outmost layer of the laminate 20. The laminate 20 may have another layer outside the outer layer 23.

In the first or second embodiment, the laminates 10 and 20 have a layer containing a cyclic olefin interpolymer (copolymer) as a resin having excellent non-sorption properties (non-adsorption properties) and moisture barrier properties. The layer containing a cyclic olefin interpolymer (copolymer) is the innermost layer 11 in the first embodiment and is the intermediate layer 22 in the second embodiment. The thickness of the innermost layer 11 or the intermediate layer 22 is preferably in a range of 50 µm to 1,000 µm and more preferably in a range of 100 µm to 400 µm. Examples of cyclic olefin copolymers (copolymers) include so-called general COPs (copolymers of different cyclic olefins), and COCs (copolymers of a cyclic olefin and an acyclic olefin). Therefore, it is possible to minimize sorption of the content to the laminates 10 and 20, improve moisture barrier properties through the laminates 10 and 20 and minimize evaporation. When evaporation through the laminates 10 and 20 is minimized, it is possible to minimize deterioration or change in concentration in the active component due to water, and it is possible to extend the expiration date of the ophthalmic solution. The thickness of the layer containing a cyclic olefin interpolymer (copolymer) may be, for example, 50 µm, 100 µm, 150 µm, 200 µm, 300 µm, 350 µm, 400 µm, 450 µm, 500 µm, 600 µm, 750 µm, or 1,000 µm, or within a range having two numerical values A and B selected from the above numerical value group as a lower limit and an upper limit (A or more and B or less).

Examples of COPs (copolymers of different cyclic olefins) include copolymers of two or more cyclic olefins and their hydrogenated products. The COP (the copolymer of different cyclic olefins) is preferably a non-crystalline polymer, and more preferably a ring-opened polymer of a cyclic olefin from metathesis or the like or its hydrogenated product. A COP (a copolymer of different cyclic olefins) has a higher proportion of an alicyclic structure than a COC (a copolymer of a cyclic olefin and an acyclic olefin) and excellent non-sorption properties (non-adsorption properties).

Examples of a COC (a copolymer of a cyclic olefin and an acyclic olefin) include copolymers of at least one cyclic olefin and at least one acyclic olefin and their hydrogenated products. The COC (a copolymer of a cyclic olefin and an acyclic olefin) is preferably a non-crystalline polymer, and more preferably a copolymer of a cyclic olefin and ethylene and its hydrogenated product.

The cyclic olefin used as a monomer constituting a cyclic olefin interpolymer (copolymer) is an unsaturated hydrocarbon (olefin) having at least one ring structure. For example, at least one of a vinyl cycloalkane including a cycloalkane having 3 to 20 carbon atoms and its derivatives, a monocycloalkene having 3 to 20 carbon atoms and its derivatives, and a cyclic olefin having a norbornene framework (a norbornene-based monomer) may be exemplified.

Examples of norbornene-based monomers include bicyclo[2.2.1]-2-heptene (norbornene) and its derivatives. Examples of norbornene derivatives include a compound having a substituent such as an alkyl group, a compound having two or more unsaturated bonds such as norbornadiene, and a compound having three or more ring structures of which two ring structures constitute a norbornene framework. Examples of norbornene-based monomers having three or more ring structures include tricyclo[$5.2.1.0^{2,6}$] decene (dihydrodicyclopentadiene), a compound in which one or more molecules of cyclopentadiene are added to norbornene or dihydrodicyclopentadiene according to a Diels-Alder reaction (for example, tetracyclododecene, pentacyclopentadecene, and hexacycloheptadecene), their hydrogenated products, and isomers thereof having double bonds at different positions, and alkyl substituents.

Examples of acyclic olefins used as monomers constituting a COC (a copolymer of a cyclic olefin and an acyclic olefin) include α-olefins such as ethylene, propylene, 1-butene, 1-pentene, 1-hexene, 1-heptene, and 1-octene, and alkenes such as 3-decene and 3-dodecene.

The resin component constituting the innermost layer 11 or the intermediate layer 22 having moisture barrier properties may be at least one of a cyclic olefin interpolymer (copolymer) alone or a mixture of a cyclic olefin interpolymer (copolymer) and other resins or the like. The proportion of the cyclic olefin interpolymer (copolymer) in the innermost layer 11 or the intermediate layer 22 is, for example, 50 weight % to 100 weight %. Examples of other resins that can be mixed into the innermost layer 11 and the intermediate layer 22 having moisture barrier properties include a polyolefin resin such as a polyethylene resin and a thermoplastic elastomer such as a styrene-based elastomer.

In the first or second embodiment, the outer layers 12 and 23 are composed of a layer containing a polyethylene resin. Thereby, it is possible to reduce the squeeze strength of the laminate having a layer containing a cyclic olefin interpolymer (copolymer) and improve squeeze properties. The thickness of the outer layers 12 and 23 may be, for example, 150 µm, 200 µm, 300 µm, 350 µm, 400 µm, 450 µm, 500 µm, 600 µm, 750 µm, 1,000 µm, 1,200 µm, or 1,400 µm, or within a range having two numerical values A and B selected from the above numerical value group as a lower limit and an upper limit (A or more and B or less). The thickness range of the outer layer 12 of the laminate 10 and the thickness range of the outer layer 23 of the laminate 20 may be different from each other.

Examples of polyethylene resins constituting the outer layers 12 and 23 include a homopolymer of ethylene (ethylene homopolymer), a linear low density polyethylene (C4-LLDPE) in which ethylene and an α-olefin having 4 carbon atoms (1-butene, etc.) are copolymerized, a linear low density polyethylene (C6-LLDPE) in which ethylene and an α-olefin having 6 carbon atoms (1-hexene, etc.) are copolymerized, a linear low density polyethylene (C8-LLDPE) in which ethylene and an α-olefin having 8 carbon atoms (1-octene, etc.) are copolymerized, an ethylene-vinyl acetate copolymer (EVA), and an ethylene vinyl alcohol copolymer (EVOH).

The resin component constituting the outer layers 12 and 23 may be at least one of a polyethylene resin alone or a mixture of a polyethylene resin and other resins or the like. The proportion of the polyethylene resin in the outer layers 12 and 23 may be, for example, 50 weight % to 100 weight %. Examples of other resins that can be mixed into the outer layers 12 and 23 include a polyolefin resin such as a polypropylene resin and a thermoplastic elastomer such as a styrene-based elastomer.

Another layer may be provided between the innermost layer 11 and the outer layer 12 in the first embodiment and between the intermediate layer 22 and the outer layer 23 in the second embodiment. If the adhesiveness between resin layers is not hindered, the innermost layer 11 or the intermediate layer 22 and the outer layers 12 and 23 may be laminated so that they are in direct contact with each other. When another layer is interposed between the innermost layer 11 or the intermediate layer 22 and the outer layers 12 and 23, its thickness is preferably, for example, 150 μm or less.

In the second embodiment, the innermost layer 21 may be a layer that does not contain a cyclic olefin interpolymer (copolymer), and may be, for example, a layer containing a thermoplastic resin such as a polyethylene resin and a polyester resin. When the innermost layer 21 is composed of a polyethylene resin, the polyethylene resin of the innermost layer 21 may be the same polyethylene resin as that of the outer layer 23 or may be a polyethylene resin different from that of the outer layer 23. The thickness of the innermost layer 21 is not particularly limited, and is, for example, 600 μm or less, and preferably 50 μm to 500 μm. Specific examples of the thickness of the innermost layer 21 may include, for example, 50 μm, 100 μm, 150 μm, 200 μm, 300 μm, 400 μm, 500 μm, or 600 μm, and may be a range having two numerical values A and B selected from the above numerical value group as a lower limit and an upper limit (A or more and B or less). The innermost layer 21 and the intermediate layer 22 may be laminated so that they are in direct contact with each other or another layer may be provided between the innermost layer 21 and the intermediate layer 22.

The thickness of the laminates 10 and 20 is preferably in a range of 300 μm to 2,000 μm and more preferably in a range of 500 μm to 1,500 μm, and may be, for example, 300 μm, 400 μm, 500 μm, 600 μm, 700 μm, 800 μm, 1,000 μm, 1,200 μm, 1,500 μm, 1,800 μm, or 2,000 μm, or within a range having two numerical values A and B selected from the above numerical value group as a lower limit and an upper limit (A or more and B or less). Here, the thickness of the laminates 10 and 20 is a total of the thicknesses of respective layers that are laminated and molded in close contact with each other over the entire surface of the accommodation part, and does not include the thickness of a layer that is partially bonded to the accommodation part such as a label or a seal or the thickness of a layer that is superimposed without close contact such as a shrink film.

The laminates 10 and 20 may have one or two or more of a reinforcing layer, a gas barrier layer, an ultraviolet absorbing layer, a print layer and the like. Examples of a method of laminating layers constituting the laminates 10 and 20 include dry laminating, extrusion laminating, coextrusion, and coating, and the method can be appropriately selected according to materials of the layers, a combination thereof and the like. The laminates 10 and 20 may be completely colorless and transparent or partially or entirely colored in the thickness direction or the plane direction. The container molding method is not particularly limited, and for example, blow molding and the like may be used. The type of the container is not particularly limited, and for example, a bottle container may be used.

The gas barrier layer can be formed of, for example, an inorganic substance or a gas barrier resin. Examples of inorganic substances include a metal deposition layer and metal oxides such as alumina. Examples of gas barrier resins include an ethylene-vinyl alcohol copolymer (EVOH), vinylidene chloride, and a fluororesin (PCTFE, PTFE, PFA). However, unlike a packaging bag and the like, the accommodation part of the ophthalmic solution container is repeatedly pressed during instillation and has a large load thereon. Therefore, the laminates 10 and 20 do not include a gas barrier layer made of heterogeneous materials such as an inorganic substance and a halogen-containing resin, but a combination having excellent mutual adhesion is adopted, and an accommodation part composed of a polyethylene resin and a cyclic olefin interpolymer (copolymer) is preferably formed.

The laminates 10 and 20 may have a layer containing an oxygen absorbent. Examples of oxygen absorbents include a conjugated diene polymer and a conjugated diene polymer cyclized product obtained by cyclizing a conjugated diene polymer, and a transition metal salt. Examples of conjugated diene polymer include polyterpenes such as poly(α-pinene), poly(β-pinene), and poly(dipentene). Examples of transition metal salts include cobalt(II) oleate, cobalt(II) naphthenate, cobalt(II) 2-ethylhexanoate, cobalt(II) stearate, and cobalt (II) neodecanoate. The layer containing an oxygen absorbent may be the above resin layers, that is, the innermost layer 11, the innermost layer 21, the intermediate layer 22 or the outer layers 12 and 23 having moisture barrier properties, or other layers.

Figure 3:
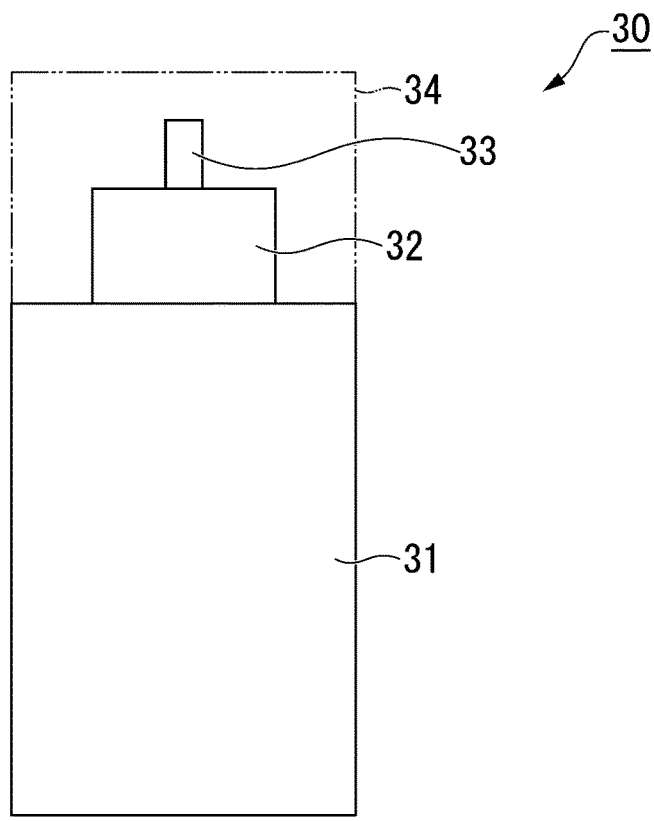
FIG. 3 is a schematic diagram showing an example of an ophthalmic solution container.

FIG. 3 is a schematic diagram showing an example of an ophthalmic solution container. An ophthalmic solution container 30 according to the present embodiment has an accommodation part 31 in which an ophthalmic solution such as a liquid is accommodated and a nozzle part 33 for instilling an ophthalmic solution accommodated in the accommodation part 31. A diameter-reduced part 32 may be provided stepwise between the accommodation part 31 and the nozzle part 33. At least the accommodation part 31 is preferably composed of the laminates 10 and 20 having the layer containing a cyclic olefin interpolymer (copolymer) and the layer containing a polyethylene resin described above.

The accommodation part 31 and the diameter-reduced part 32 may be integrally formed of the laminates 10 and 20. When the accommodation part 31 and the diameter-reduced part 32 are integrally formed, the nozzle part 33 may have a portion fitted into the diameter-reduced part 32. When the accommodation part 31 and the diameter-reduced part 32 are formed separately, the nozzle part 33 is integrally formed with the diameter-reduced part 32, and the diameter-reduced part 32 may have a portion fitted to the upper part of the accommodation part 31.

The ophthalmic solution container 30 may have a cap 34 for protecting the nozzle part 33. The cap 34 is preferably connected to at least one of the accommodation part 31, the diameter-reduced part 32, and the nozzle part 33 in an openable or detachable manner. The capacity of the accommodation part 31 is not particularly limited, and may be, for example, 50 ml or less, and may be 1 ml, 2.5 ml, 3 ml, 5 ml, 10 ml, 15 ml, 20 ml, 25 ml, 30 ml, 40 ml, or the like, or within a range having two numerical values A and B selected from the above numerical value group as a lower limit and an upper limit (A or more and B or less).

Examples of ophthalmic solutions include an aqueous ophthalmic solution, an oil-based ophthalmic solution, an ophthalmic solution that is soluble when used, and a suspension ophthalmic solution. The ophthalmic solution may contain, as additives other than the active component, one or two or more of a solubilizing agent, a stabilizing agent, an isotonizing agent, a buffering agent, a pH adjusting agent, a preservative, and a thickener.

Specific examples of active components used in the ophthalmic solution are not limited, and may include isopropyl unoprostone, latanoprost, travoprost, tafluprost, and bimatoprost as prostaglandin-related drugs; diclofenac sodium, pranoprofen, bromfenac sodium hydrate, and nepafenac as non-steroidal anti-inflammatory drugs; cyanocobalamin, and flavin adenine dinucleotide sodium as vitamin B formulations; acitazanolast hydrate, amlexanox, ibudilast, epinastine hydrochloride, olopatadine hydrochloride, sodium cromoglycate, ketotifen fumarate, tranilast, pemirolast potassium, and levocabastine hydrochloride as antiallergic components; cyclosporine and tacrolimus hydrate as immunosuppressants; carteolol hydrochloride, timolol maleate, nipradilol, betaxolol hydrochloride, and levobnorol hydrochloride as β blockers; bunazosin hydrochloride as α1 blockers; brimonidine tartrate as α2 stimulants; pilocarpine hydrochloride as parasympathomimetic agents; dipivefrine hydrochloride as sympathomimetic agents; distigmine bromide as cholinesterase inhibitors; glutathione and pirenoxine as cataract remedies; gatifloxacin hydrate, dibekacin sulfate, tosufloxacin tosylate hydrate, tobramycin, vancomycin hydrochloride, moxifloxacin hydrochloride, levofloxacin hydrate, lomefloxacin hydrochloride, ofloxacin, chloramphenicol, and norfloxacin as antibacterial drugs; and dorzolamide hydrochloride and brinzolamide as β blocker/carbonic anhydrase inhibitor combination agents. One or two or more thereof may be contained.

While the present invention has been described above based on preferred embodiments, the present invention is not limited to the above embodiments, and various modifications can be made without departing from the spirit and scope of the present invention.

The packaging container composed of the laminate of the present embodiment is not limited to an accommodation part of an ophthalmic solution container and can be applied to a container in which other contents are accommodated. For example, nasal drops, ear drops, and other drugs in a form in which a drug solution is dropped onto an affected part during administration may be exemplified.

In the layer containing a cyclic olefin interpolymer (copolymer), it is possible to incorporate a cyclic olefin homopolymer or its hydrogenated products in place of the cyclic olefin interpolymer (copolymer), or together with the cyclic olefin interpolymer (copolymer).

EXAMPLES

Hereinafter, the present invention will be described in detail with reference to examples.
(Measurement of Squeeze Strength and Water Vapor Transmission Rate of Ophthalmic Solution Container)

According to the layer configuration shown in Table 1, the accommodation part of the ophthalmic solution container was molded into a bottle by blow molding. The shape of the accommodation part had a cylindrical shape (round shape) having a diameter of 20 mm and a height of about 27 mm, and had a bottom at the lower part and a mouth part at which a nozzle was mounted at the upper part.

In the column "thickness [μm]" in Table 1, when the material and thickness of one layer straddle the columns "outer layer" and "intermediate layer," this indicates that this layer is the outer layer of the first embodiment in which the intermediate layer is omitted. In addition, when the material and thickness of one layer straddle the columns "outer layer," "intermediate layer" and "innermost layer," this indicates that the material is a single layer.

"PE1" indicates a polyethylene resin (density 931 [Kg/m$^3$], MFR 1.1 [g/10 min]), "PE3" indicates a polyethylene resin (density 922 [Kg/m$^3$], MFR 0.6 [g/10 min]), and "PE4" indicates a polyethylene resin (density 931 [Kg/m$^3$], MFR 1.1 [g/10 min]). In addition, "C1" indicates a cyclic olefin interpolymer (copolymer) (density 1,010 [Kg/m$^3$], MFR 9.0 (230° C.) [g/10 min]), and "C2" indicates a cyclic olefin interpolymer (copolymer) (density 1,010 [Kg/m$^3$], MFR 20.0 (280° C.) [g/10 min]). In addition, "CE" indicates a mixture of "C1" and a styrene-based elastomer (density 1,000 [Kg/m$^3$], MFR 8.3 (230° C.) [g/10 min]). A total of thicknesses shown in Table 1 indicates the thickness of the laminate, but each value is an average value, and thus a total of the thicknesses of the layers does not match the thickness of the laminate (with an error of ±1 μm or less) in some cases.

For the squeeze strength (N), a metal ball having a diameter of 10 mm was applied to the central part of the bottle at a speed of 100 mm/min (a rate of being compressed 2 mm in 1.2 sec), and the maximum load was measured when the wall of the bottle was compressed by 3 mm. The directions in which a ball was applied to the bottle were four directions including up, right, down, and left, measurement was performed with the number of evaluations n=5, and an average value was determined.

A method of measuring a water vapor transmission rate was as follows: (1) the weight of the empty bottle was measured, (2) the bottle was filled with 5.0 ml of distilled water and an aluminum constituent film was then used as a lid, (3) the weight of the bottle after filling was measured, and then stored under an environment of a temperature 40° C. and a humidity RH of 25%, (4) the bottle weight was measured after a predetermined number of days had elapsed, and (5) the water vapor transmission rate [%] was calculated. The measurement was performed with the number of evaluations n=5, and an average value was determined. In this test, the water vapor transmission rate was a value obtained by calculating the rate of weight loss (reduction in weight) as in the first method of the water vapor transmission test according to Japanese Pharmacopoeia, but the temperature was higher and the humidity was lower in measurement conditions. Here, it was thought that, since the aluminum constituent film had sufficiently lower water vapor transmission than the bottle, transmission of water vapor through the lid was negligible.

TABLE 1

| | Thickness [μm] | | | | Squeeze strength [N] | | | | | Water vapor transmission rate [%] (40° C., 25% RH) | | | |
|---|---|---|---|---|---|---|---|---|---|---|---|---|---|
| | Outer layer | Intermediate layer | Innermost layer | Total | Average | Up | Right | Down | Left | 7 days | 30 days | 60 days | 90 days |
| Example 1 | PE1 415 | C1 122 | PE1 132 | 668 | 15.1 | 14.7 | 14.6 | 15.6 | 15.6 | 0.12 | 0.53 | 1.04 | 1.56 |
| Example 2 | PE1 359 | C1 181 | PE1 124 | 663 | 20.1 | 21.6 | 20.7 | 19.1 | 19.1 | 0.07 | 0.31 | 0.61 | 0.91 |
| Example 3 | PE1 440 | C1 85 | PE1 111 | 636 | 15.8 | 16.8 | 15.6 | 15.0 | 16.0 | 0.10 | 0.43 | 0.84 | 1.25 |
| Example 4 | PE1 480 | C1 89 | PE1 105 | 675 | 18.1 | 17.9 | 18.1 | 18.5 | 17.9 | 0.10 | 0.40 | 0.79 | 1.19 |
| Example 5 | PE1 368 | C1 69 | PE1 100 | 537 | 10.5 | 10.3 | 11.1 | 10.8 | 9.7 | 0.13 | 0.54 | 1.08 | 1.61 |
| Example 6 | PE1 439 | CE 179 | PE1 162 | 780 | 23.9 | 24.2 | 25.8 | 23.8 | 21.9 | 0.08 | 0.32 | 0.64 | 0.95 |

TABLE 1-continued

|  | Thickness [μm] | | | | Squeeze strength [N] | | | | | Water vapor transmission rate [%] (40° C., 25% RH) | | | |
|---|---|---|---|---|---|---|---|---|---|---|---|---|---|
|  | Outer layer | Intermediate layer | Innermost layer | Total | Average | Up | Right | Down | Left | 7 days | 30 days | 60 days | 90 days |
| Example 7 | PE1 368 | C2 114 | PE1 105 | 587 | 14.0 | 13.6 | 15.3 | 14.5 | 12.5 | 0.12 | 0.51 | 1.01 | 1.51 |
| Example 8 | PE4 386 | C1 96 | PE4 105 | 587 | 12.0 | 11.8 | 11.3 | 12.4 | 12.7 | 0.11 | 0.45 | 0.87 | 1.29 |
| Comparative Example 1 | PP 392 | | | 392 | 13.0 | 11.1 | 15.0 | 14.3 | 11.8 | 0.18 | 0.78 | 1.54 | 2.29 |
| Example 9 | PE4 531 | | C1 79 | 610 | 17.2 | 17.1 | 18.7 | 17.0 | 16.1 | 0.11 | 0.45 | 0.86 | 1.26 |
| Example 10 | PE4 554 | | C1 92 | 645 | 19.8 | 20.3 | 20.9 | 18.9 | 19.1 | 0.10 | 0.41 | 0.78 | 1.12 |
| Example 11 | PE4 480 | | C1 63 | 543 | 12.7 | 13.8 | 13.4 | 11.5 | 12.1 | 0.13 | 0.52 | 1.00 | 1.45 |
| Example 12 | PE1 513 | | C1 82 | 595 | 17.0 | 16.9 | 18.4 | 16.9 | 15.8 | 0.11 | 0.47 | 0.92 | 1.34 |
| Example 13 | PE1 597 | | C1 72 | 669 | 20.7 | 20.7 | 22.8 | 20.7 | 18.8 | 0.09 | 0.42 | 0.83 | 1.22 |
| Example 14 | PE3 534 | | C1 116 | 650 | 15.4 | 14.9 | 17.1 | 15.8 | 13.9 | 0.11 | 0.46 | 0.89 | 1.29 |
| Example 15 | PE4 516 | | C2 109 | 624 | 17.7 | 17.0 | 18.8 | 15.7 | 19.5 | 0.11 | 0.48 | 0.93 | 1.35 |

As shown in Table 1, according to the ophthalmic solution containers of Examples 1 to 15, it was confirmed that the squeeze strength was comparable to that of the conventional product (Comparative Example 1), and the water vapor transmission rate was superior to that of the conventional product (Comparative Example 1) over the long term.

(Adsorption Test of Ophthalmic Solution Container)

In the ophthalmic solution container of Example 16, the innermost layer sealant was made of a cyclic olefin, and a polyethylene (PE) layer was used on the outside thereof. The shape, size, production method, and the like of the ophthalmic solution container used for the adsorption test were the same as those of the ophthalmic solution container used for measuring the squeeze strength and water vapor transmission rate described above. In the column "thickness [μm]" in Table 2, the layer configuration is described as in Table 1.

The adsorption test was performed by measuring the residual concentration of the active component after the ophthalmic solution container in which the ophthalmic solution was accommodated was stored under predetermined conditions.

The ophthalmic solution was prepared by dissolving 50 mg of an active component latanoprost (reagent) in a mixed solvent (acetonitrile 5%, distilled water, polysorbate 20) so that the concentration was about 500 ppm and then adjusting the concentration of latanoprost to about 0.005% with respect to the volume which was produced. About 5 ml of this ophthalmic solution was put into a bag-shaped ophthalmic solution container using a whole pipette, and stored under a dry environment at 40° C., and when the storage period from inclusion was 28 days or 60 days, the residual concentration in the ophthalmic solution in the container was measured. 28 days is 672 hours, and 60 days is 1,440 hours.

For the residual concentration, in liquid chromatography, the mobile phase was a mixed solution containing 0.2% acetic acid aqueous solution:acetonitrile=48:52, the flow rate was 1.0 ml/min, the measurement wavelength of the absorbance was 210 nm, the column temperature was 40° C., the column (ODS column, C18 column, 4.6 mm×250 mm, 5 μm) was used, the retention time was about 18 minutes, and the concentration of the active component was measured from the value of the absorbance.

The ophthalmic solution before being placed in the ophthalmic solution container had a storage period of 0 weeks, and the residual concentration at that time was set as the initial concentration. The measured value of the initial concentration was 68.9 ppm. The residual ratio (%) was calculated as a ratio of the residual concentration to the initial concentration according to the following formula.

Residual ratio (%)=[residual concentration (ppm)]/[initial concentration (ppm)]×100(%)

TABLE 2

| Initial concentration: 68.9 ppm | | | | | | | | |
|---|---|---|---|---|---|---|---|---|
| | Thickness [μm] | | | | | After 0 days | After 28 days | After 60 days |
| | Outer layer | Intermediate layer | Innermost layer | Total | Storage period | | | |
| Comparative Example 1 | PP 392 | | | 392 | Residual concentration (ppm) | 68.9 | 65.5 | 60.5 |
| | | | | | Residual ratio (%) | 100 | 95.0 | 87.8 |
| Example 16 | PE4 519 | | C2 210 | 729 | Residual concentration (ppm) | 68.9 | 66.8 | 65.4 |
| | | | | | Residual ratio (%) | 100 | 96.9 | 94.9 |

As shown in Table 2, according to the ophthalmic solution container of Example 16, improved non-adsorption properties with respect to the active component were exhibited.

INDUSTRIAL APPLICABILITY

As described above, according to the ophthalmic solution container of the present invention, it is possible to minimize sorption (adsorption and absorption) of the ophthalmic solution, improve moisture barrier properties and minimize evaporation, and also reduce the squeeze strength and improve squeeze properties, and thus the present invention can be used industrially.

REFERENCE SIGNS LIST 10, 20 Laminate
11 Moisture-proof innermost layer
12, 23 Outer layer
21 Innermost layer
22 Intermediate layer
30 Ophthalmic solution container
31 Accommodation part
32 Diameter-reduced part
33 Nozzle part
34 Cap

What is claimed is:

1. An ophthalmic solution container having an accommodation part in which an ophthalmic solution is accommodated,
    wherein the accommodation part is composed of a laminate having an innermost layer that does not contain a cyclic olefin interpolymer (copolymer) and contains a polyethylene resin, an intermediate layer containing a cyclic olefin interpolymer (copolymer) provided outside the innermost layer, and an outer layer containing a polyethylene resin provided outside the intermediate layer containing the cyclic olefin interpolymer (copolymer),
    wherein a thickness of the intermediate layer containing the cyclic olefin interpolymer (copolymer) is 50 μm to 1,000 μm, a thickness of the outer layer containing a polyethylene resin is 350 μm to 1,400 μm, a thickness of the innermost layer is 162 μm or less, and a thickness of the laminate is 500 μm to 2,000 μm.

2. The ophthalmic solution container according to claim 1,
    wherein the thickness of the intermediate layer containing the cyclic olefin interpolymer (copolymer) is 69 μm to 181 μm, and the thickness of the outer layer containing a polyethylene resin is 359 μm to 480 μm.

3. The ophthalmic solution container according to claim 1,
    wherein the ophthalmic solution container has a nozzle part for instilling an ophthalmic solution accommodated in the accommodation part.

4. The ophthalmic solution container according to any one of claim 1,
    wherein the intermediate layer containing the cyclic olefin interpolymer (copolymer) contains at least one of a COP (a copolymer of different cyclic olefins) or a COC (a copolymer of a cyclic olefin and an acyclic olefin).

* * * * *